United States Patent [19]

Johnson et al.

[11] Patent Number: 5,112,752
[45] Date of Patent: May 12, 1992

[54] BIOCATALYTIC OXIDATION USING SOYBEAN AND OTHER LEGUME PEROXIDASES

[75] Inventors: Mark A. Johnson, Chillicothe; Alexander R. Pokora, Pickerington; William L. Cyrus, Jr., Ray, all of Ohio

[73] Assignee: The Mead Corporation, Dayton, Ohio

[21] Appl. No.: 704,073

[22] Filed: May 22, 1991

Related U.S. Application Data

[62] Division of Ser. No. 599,584, Oct. 18, 1990.

[51] Int. Cl.$^5$ ............................ C12N 9/08; C12P 7/22
[52] U.S. Cl. .................................. 435/192; 435/156; 435/800; 435/814; 435/816; 435/911
[58] Field of Search ............... 435/192, 911, 800, 814, 435/816, 156

[56] References Cited

U.S. PATENT DOCUMENTS

| | | | |
|---|---|---|---|
| 3,616,235 | 1/1971 | Schoepfel et al. | 435/202 |
| 3,769,168 | 10/1973 | Masuda et al. | 435/201 |
| 3,947,324 | 3/1976 | Lakshminarayanan | 435/192 |
| 4,090,919 | 5/1978 | Chibata et al. | 435/178 |
| 4,328,312 | 5/1982 | Tsurumi et al. | 435/192 |
| 4,585,738 | 4/1986 | Roland | 435/177 |
| 4,698,306 | 10/1987 | Noda et al. | 435/192 |
| 4,737,460 | 4/1988 | Shinmen et al. | 435/192 |
| 4,910,135 | 3/1990 | Tischer et al. | 435/177 |
| 4,992,372 | 2/1991 | Pokora et al. | 435/192 |

*Primary Examiner*—Herbert J. Lilling
*Attorney, Agent, or Firm*—Thompson, Hine and Flory

[57] ABSTRACT

Biocatalytic oxidative processes wherein oxidizable substrates are reacted with peroxides in the presence of a peroxidase such as soybean peroxidase or another legume peroxidase; an oxidative coupling reaction for producing phenolic resins; a method for the purification of peroxidase enzyme-containing extracts generally also are described.

3 Claims, No Drawings

5,112,752

BIOCATALYTIC OXIDATION USING SOYBEAN AND OTHER LEGUME PEROXIDASES

This is a division of application U.S. Pat. No. 07/599,584 filed Oct. 18, 1990.

BACKGROUND OF THE INVENTION

The present invention relates to an improved biocatalytic process for the preparation of phenolic resins using soybean peroxidase and more generally to a biocatalytic process for oxidizing phenols and other compounds using soybean peroxidases.

The present invention further relates to a method for treating peroxidase enzymes so that they may be used in applications where the untreated enzyme could not previously be employed More particularly, it relates to a method for treating a peroxidase enzyme source with a purifying agent to reduce the amount of impurities in the enzyme and thereby reduce contamination in processes using such enzymes as a biocatalyst.

U.S. Pat. No. 4,900,671 commonly assigned to the Mead Corporation discloses a method for preparing a phenolic resin which comprises preparing a solution of a phenol in a water miscible or immiscible solvent and an aqueous solution of a peroxidase or oxidase enzyme, mixing the two solutions and adding a peroxide or oxygen. The preferred method described in this patent makes use of horseradish peroxidase The reaction is preferably carried out in a mixed solvent system. The peroxidase is dissolved in water, the phenol is dissolved in a solvent which may be water miscible or water immiscible. Hydrogen peroxide is added to the system and reaction occurs on the enzyme. It has now been found that soybean peroxidase is much more economical to use in this method It has also been found that the quality of resin obtained from this method can be improved if the peroxidase is treated as described herein.

Alberti and Klibanov, BIOLOGICAL DETOXICATION, Chapter 22, Peroxidase for Removal of Hazardous Aromatics from Industrial Wastewaters, (1982), discloses that phenols can be removed from wastewaters as high molecular weight polymers by the action of peroxidase enzymes. The disclosed method relies on the ability of peroxidase enzyme to catalyze, with hydrogen peroxide, the oxidation of a variety of phenols and aromatic amines. Phenolic and aromatic amine free radicals are generated, which diffuse from the active center of the enzyme into solution, and polymerize to polyaromatic products. These high molecular weight polymers are water-insoluble and can be readily separated by filtration from water.

In the past, peroxidase enzymes have not been available at a cost and in a purity amenable to many biocatalytic processes. For example, horseradish roots, a common source of horseradish peroxidase, are cultivated generally in small quantities and are propagated through root cuttings, thus making it difficult to scale up production. The limited availability of the horseradish root extract coupled with the shortage of alternative sources of enzyme has created a very expensive market for such enzymes. Accordingly, there exists in the marketplace a need for an abundant and relatively inexpensive source of peroxidase.

SUMMARY OF THE INVENTION

A principal object of the present invention is to improve the biocatalytic oxidative process for preparing phenolic resins described in U.S. Pat. No. 4,900,671 through the use of peroxidases from soybeans and other legumes and plants. It has been found that soybean peroxidase has better temperature and solvent stability than horseradish peroxidase and that it is much more economical because it can be obtained from soybean hulls which are very inexpensive. This finding suggests that peroxidase from other sources and particularly legumes may also be advantageously used in the process.

A more general object of the present invention is to provide biocatalytic oxidative processes using soybean peroxidase or peroxidases from other legumes, rice, and plants (e.g., malvaceous plants such as cotton, see Egley, G. H., et al., Planta 157:224-232 (1983)). One such oxidative process is oxidative coupling of phenols and aromatic amines, however, there are other oxidative processes in which peroxidases have been used in which soybean peroxidase and other plant and legume peroxidases can be advantageous including wastewater treatment, oxidation of aromatic amines and others.

Still another object of the invention is to provide novel processes for biocatalytic oxidation wherein oxidation is carried out in the presence of the hulls of a legume which produces peroxidase, a particularly preferred legume hull is soybean hulls. It has been found that in many cases it is not necessary to remove peroxidase from the hull by extraction but that the hull can be directly introduced to the reaction medium where the peroxidase is available as an immobilized enzyme or by in situ extraction to catalyze the oxidative process.

Another object of the invention is to improve biocatalytic processes employing peroxidases by treating the peroxidase to remove non-peroxidase proteins and other lipophilic materials. These contaminants interfere with many biocatalytic processes by discoloring the reaction product. They can also lead to emulsification of the reaction system when the reaction is performed in aqueous media making it difficult to control the molecular weight and molecular weight distribution of the product and making it difficult to separate the product (See Example 2). In accordance with one aspect of the invention, peroxidase as a solution in water, is treated with protein fixatives or detergents to remove the unwanted materials. In another method, the peroxidase is treated with activated carbon.

Accordingly, one manifestation of the present invention is an improved process of biocatalytic oxidation wherein an oxidizable substrate is reacted with a peroxide in the presence of a peroxidase wherein the peroxidase is a peroxidase of a legume (plants of the family Leguminoseae) and, more particularly, soybean peroxidase, rice, or a plant of the family Malvaceae.

Another manifestation of the present invention is a process for preparing a phenolic resin which comprises reacting a phenol with soybean peroxidase or another of the aforementioned peroxidases in the presence of a peroxide. In a preferred embodiment of the invention, this reaction is carried out in a mixed solvent of water and a water miscible or a water immiscible solvent. In another embodiment of the invention, the peroxidase is supplied to the reaction as soybean or other legume hulls. Other embodiments of the invention utilize peroxidases from rice and malvaceous plants such as cotton.

Another manifestation of the invention is a process for treating peroxidase to remove proteinaceous or lipophilic contaminants and render it more useful in biocatalytic processes which comprises preparing a solution of a peroxidase and a protein fixative or a detergent, adding a non-solvent for the peroxidase, re-dissolving the peroxidase and separating the peroxidase from the contaminants.

In another embodiment of the invention, the peroxidase is purified by making a slurry of a peroxidase solution with activated carbon and removing the activated carbon.

Other objects and advantages will be apparent from the following description and the appended claims.

DEFINITIONS

The term "phenolic resin" as used herein includes phenolic dimers and trimers as well as higher molecular weight species.

A "unit" of peroxidase means the amount of peroxidase which produces a change of 12 absorbance units measured at 1 cm pathlength in one minute at 420 nm when added to a solution containing 100 mM potassium phosphate, 44 mM pyrogallol and 8 mM hydrogen peroxide and having a pH of 6 (Sigma Chemical Co. Peroxidase Bulletin).

DETAILED DESCRIPTION OF THE INVENTION

In the preferred embodiments of the invention, the peroxidase is soybean peroxidase, however, peroxidases from other legumes are also useful such as peroxidases from peas, guar beans, garbanzo beans, runner beans and the non-legume, rice. It is also believed that peroxidases from certain malvaceous plants such as cotton may be useful. The purification techniques described herein, in addition to being effective for peroxidases extracted from legumes, rice and malvaceous plants are also useful with horseradish peroxidase, haloperoxidases including chloroperoxidases, lactoperoxidases, bacterial peroxidases, and fungal ligninase.

Peroxidases, being water soluble, are easily harvested by homogenizing the protein source with water, filtering the homogenate, and retaining the filtrate.

The filtrate is treated to remove proteinaceous and lipophilic impurities by adding to the filtrate a solution of a protein fixative or a detergent and forcing the enzyme to precipitate by the addition of a non-solvent for the peroxidase such as acetone or isopropanol. The protein fixative and detergent both preferentially render the protein contaminants insoluble in water. The detergent also insolublizes nonprotein lipophilic impurities. After addition of the fixative or detergent, a non-solvent for peroxidase is added to the solution to force the peroxidase and impurities to precipitate. The precipitate is separated, water is added to redissolve preferentially the peroxidase and the sample is centrifuged. The peroxidase is recovered as the supernatant solution While these treatments probably do not completely remove impurities, they reduce them to a level that the oxidation product obtained using the peroxidase is improved in quality.

When using the detergent, the precipitate is preferably treated with a solution of phenol and a small amount of hydrogen peroxide. This appears to cause the phenol to interact with the detergent and enhance the binding of the impurities. After about one hour the sample is centrifuged to remove the impurities. The peroxidase is recovered in the supernatant solution These processes may be repeated to further purify the enzyme.

The protein fixatives useful in treating the peroxidase include tannic acid, tannins, monolignols, fulvic acids, lignan, humic acids, melanoidins, proanthcyanidins, stilbenes, depsides, lignin model compounds, soluble suberin, flavonoids, soluble lignin, dihydroxyphenyl compounds, kerogen, gallic acid esters, phenolic acids, gallic acid amides, dihydric phenols, hexahydroxydiphenic glucose esters, polymeric phenols, bis (hydroxyphenyl) sulfones, bitumens, soluble lignite extracts, sulfonated phenols and naphthols and their copolymers, melamine/glyoxal/glyoxylate/phenol/naphthol condensates; vegetable extractives, especially rhubarb, mimosa, peat, euphorbia, cassia, rose, tea, grape and saxifragea; sulfonated extractives, especially of mimosa wood; and bark extractives, such as oak, eucalyptus, fig, cedar, spruce, pine, walnut, mulberry and chestnut; and graft copolymers derived from these extracts Others include synthetic phenolic tanning agents (syntans) such as tanigan, tamol, ledertan, blancotan, basyntan, neosyn and nubuctan and phenolic compounds that cause melanization or sclerotization of proteins, especially catechol and dopamine amides, quinones, quinone methides, prenylated phenols and quinones and polymers derived from their oxidation, e.g., melanins and sclerotins, and the like.

Useful detergents include sodium dodecyl sulfate, sodium caprylate, sodium cholate, sodium decanesulfonic acid, sodium deoxycholate, sodium glycocholate, sodium deoxyglycocholate, sodium taurocholate, sodium taurodeoxycholate, cetylpyidinium chloride, dodecyltrimethyl ammonium, CHAPS, CHAPSO, dioctyl sulfosuccinate, alginic acid. Phenols useful to enhance detergent purification include t-butylphenol and bisphenols such as bisphenol A.

Removal of the impurities can be enhanced by adding a salt such as potassium chloride to the aqueous solution of the enzyme in an amount of about 1 to 10%. For certain protein fixatives such as the phenols which are not soluble in water, a small amount of a solvent such as an alcohol may be used to dissolve these fixatives in water as shown in Examples 5-9 below.

Non-solvents of the peroxidase are used to force the enzyme to precipitate and enable its separation. Useful nonsolvents may be water miscible or water immiscible, however, they are preferably water miscible. Representative examples include acetone, isopropanol, n-propanol, methanol, and ethanol.

To purify the enzyme, peroxidase is added to water in an amount of about 400 units per ml water. When the protein fixative is used, it is generally added to the enzyme solution in an amount of about 1% to 10% based on weight of fixative to volume of enzyme (kg. to 1). Similar amounts of detergent are employed. The volume of the non-solvent which must be added to the enzyme solution to separate the enzyme will vary with the nature of the non-solvent but generally 1 to 10 volumes of nonsolvent per volume of enzyme solution is required.

One oxidative process for preparing phenolic resin in accordance with the present invention comprises preparing separate solutions of the phenol, enzyme, and peroxide, and mixing them. The phenol is typically dissolved in an organic solvent, and the enzyme and peroxide are typically dissolved in water. The solutions may be gradually added to a common reaction vessel, but in a preferred method solutions of the phenol and the enzyme are pre-mixed and the peroxide solution is gradually added thereto. The enzyme may also be provided on a solid support or legume hulls may be used directly. The process may be carried out on a batch or continuous basis. In any process it is important to limit the rate of addition of the peroxide since excess peroxide tends to inhibit the reaction.

The amount of the enzyme used to make the phenolic resin will depend on its activity. The enzyme is not consumed in the reaction but gradually loses activity during the course of reaction. For practical purposes, the enzyme can be reacted in an amount of about 500 to 500,000 and more typically 1000 to 5000 units per 100 grams phenol. In other oxidative reactions, analogous amounts of the peroxidase will be used.

The peroxide used is typically hydrogen peroxide, but other peroxides are also useful. Examples of other potentially useful peroxides include methyl peroxide, ethyl peroxide, etc.

The peroxide is reacted in an amount of about 0.1 to 2.5 moles per mole phenol (or other oxidizable substrate) and, more typically, about 0.1 to 1.0 moles per mole phenol. Depending upon the nature of the oxidizing agent, it is reacted neat or as a solution The preferred oxidizing agent, hydrogen peroxide, is dissolved in water. Its concentration may range form about 1 mM to 10 M.

Phenols can be reacted in a water-miscible or a waterimmiscible solvent Representative examples of useful waterimmiscible solvents include hexane, trichloromethane, methyl ethyl ketone, ethyl acetate, and butanol. Examples of useful water-miscible solvents include ethanol, methanol, dioxane, tetrahydrofuran (THF), dimethyl formamide, methyl formate acetone, n-propanol, isopropanol, ethanol, t-butyl alcohol. The reaction is typically carried out at phenol concentrations of about 1 to 100 g per 100 ml solvent.

A number of different procedures may be used to react the phenol or other oxidizable substrate. Solutions of the phenol, enzyme, and peroxide may be individually prepared and metered into a reaction vessel, or solutions of the phenol and enzyme may be pre-mixed and the peroxide gradually added thereto. Alternatively, the enzyme and the phenol may be dissolved in a common solvent and the peroxide added later. Those skilled in the art will appreciate that a number of different reaction/mixing sequences are useful. The peroxide should be added at a controlled rate which is approximately equal to the rate at which it is consumed such that the concentration of the peroxide does not build to a level at which it undesirably inhibits the reaction and inactivates the enzyme.

The organic-aqueous system formed upon mixing the phenol, enzyme and peroxide may contain water and an organic solvent in a volumetric ratio (water:organic) in the range of about 1:10 to 10:1, more typically, 1:2 to 2:1. The most preferred ratio will vary with the nature of the phenolic monomer(s) that is (are) polymerized.

As indicated earlier, the legume hulls are biocatalytically active and can be used directly. It is not clear whether the peroxidase is being extracted by the reaction solvent medium or whether the peroxidase reacts similar to an immobilized enzyme. A combination of both mechanisms may occur.

The amount of hulls used will depend on their reactivity. To prepare the hulls for the reaction, they are preferably crushed and washed with toluene and added to ammonium sulfate solution as illustrated in Example 14 below. Aged hulls may work as well as fresh ones. The reaction may be carried out by simply preparing a slurry of the hulls in an aqueous solution of the phenol and gradually adding peroxide thereto at a controlled rate which does not result in reaction inhibition. Alternatively, the hulls can be packed in a column and peroxide and the oxidizable substrate passed over them to yield the oxidized product.

Variations in the way the hulls are prepared produce color developer resins with either low or high natural color. Hulls added to 840 ml 0.2 to 0.4M ammonium sulfate or sodium sulfate produced much lighter resin. Hulls washed with toluene then ethyl acetate and added to ammonium or sodium sulfate solution produced still lighter resin. These same observations were made with soluble soybean peroxidase and solvent-washed hulls. The use of solvent-washed hulls and polymerization with the enzyme in 0.4M ammonium sulfate produces low-color resins. The sulfate presumably reduces color by salting-in the colored impurities in the enzyme, preventing their release to the organic phase containing the polymer. Washing the hulls removes many of these color-causing impurities prior to the reaction.

The additional thermal stability of peroxidase from soybean hulls was demonstrated by heating soybeans at 90° C. for 30 minutes. Peroxidase activity measured following extraction from the resulting hulls was the same per gram hull in the 90° C. treated sample as the untreated control. Further, polymerization of bisphenol A in 45% n-propanol with soybean peroxidase produces a low-monomer color developer up to 45° C. reaction temperature at 50 units per gram monomer. The same reaction with Finnsugar or Sigma horseradish peroxidase succeeds only up to 20° C. Further, the reaction with soybean peroxidase succeeds at one-fourth the activity level required with horseradish peroxidase at 25° C.

Reaction temperature will vary with the substrate and the enzyme, most enzymes are temperature sensitive and a temperature should be selected which does not inhibit the reaction.

The reaction of the phenol proceeds at room temperature, but temperatures of about 0° to 70° C. can be used. The enzymes are temperature sensitive and can lose their activity if the reaction temperature becomes too high. However, some latitude exists, depending upon the solvent system which is used. Certain solvents can stabilize the enzyme and thereby permit the use of higher temperatures. There is evidence in the literature that temperatures up to 100° C. may be useful with some peroxidases.

The activity of peroxidases is pH dependent. The oxidative reactions are typically carried out at a pH in the range of 4 to 12 and, preferably, 4 to 9, and, more preferably, about 6. A pH may be selected at which the enzyme is highly active. This will vary with the nature of the enzyme and its source. Buffers can be used to maintain pH, but are not usually required. One example of a useful buffer is a potassium phosphate buffer.

While reference is herein made to the bulk pH of the reaction system, those skilled in the art will appreciate that it is the pH in the micro-environment of the enzyme that is critical. Thus, where the phenol is dissolved in a water immiscible solvent and the enzyme solution is dispersed in the solution of the phenol, it is the pH of the enzyme solution which is critical.

Phenolic resins prepared in accordance with the present invention are useful in a variety of applications depending on the nature of the phenol and the molecular weight distribution of the resin. The resins are often mixtures of dimers, trimers, and higher molecular weight oligomers.

The molecular weight of the phenolic resin can be adjusted depending upon its particular end use. In one embodiment, the process of the present invention provides a phenolic resin which is useful as a developer in recording materials such as carbonless copy paper, heat-sensitive recording paper, electrothermographic recording paper and the like. The phenols used in developer resins are preferably para-substituted. Developer resins may range from about 500 to 5000 in molecular weight.

In another embodiment, the process of the present invention provides a phenolic resin which is useful as an adhesive. The phenols used in adhesives need not be parasubstituted. The resins typically range from about 1000 to 15,000 in molecular weight but molecular weights up to at least 30,000 are attainable. Among other factors affecting molecular weight are solvent selection, phenol selection, and reaction conditions.

Phenols which are preferred for reaction in the present invention are represented by the Formula (I):

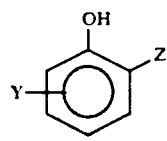

(I)

wherein Y and Z are selected from the group consisting of a hydrogen atom, a halogen atom, an alkyl group, an alkoxy group, an aryl group, an allyl group, a phenylalkyl group, a —COOR group, a —NR$^1$R$^2$ group, where R represents a hydrogen atom or a lower alkyl group, and R$^1$ and R$^2$ represent a hydrogen atom, an alkyl group, or a phenylalkyl group or Z in conjunction with the adjacent meta position forms a condensed benzene ring. Since polymerization proceeds via the ortho or para positions, when Y is at the ortho or para position, at least one of Y and Z must be a hydrogen atom or Z must form said condensed benzene ring. Y is preferably para to the phenolic hydroxyl group. Otherwise, the phenol adds as a terminal group as discussed below. At the para position, long chain alkyl groups have a tendency to slow the reaction. The reaction appears to proceed best when Y is p-phenyl, p-methoxy or p-halogen.

A single phenol or a mixture of phenols may be used in the process of the present invention. In certain applications it may be desirable to produce phenolic resins having certain terminal groups. This can be accomplished by reacting phenols in which the Y substituent is in the para position and Z is not a condensed ring with other phenols in which at least one of Y and Z is a hydrogen atom or Z is a condensed ring to provide copolymers. In this case the resin contains the Z substituent as a terminal group. When the para position is unsubstituted, polymerization proceeds via the ortho and/or para position and Z-substituted phenols can be incorporated mid-chain.

The alkyl group represented by Y and Z may contain up to 10 carbon atoms and include such alkyl groups as t-butyl, n-butyl, octyl, nonyl, etc. When R, R$_1$, and R$_2$ represent an alkyl group, it is typically a lower alkyl group having 1 to 4 carbon atoms.

Representative examples of alkoxy groups for Y and/or Z have 1 to 10 carbon atoms and include methoxy and ethoxy. When Y or Z is an aryl group, it is typically a phenyl group or substituted phenyl group such as a halogen-substituted phenyl group, an alkyl-substituted phenyl or a phenol group such as a 4'-phenol group.

Examples of a halogen atom include fluorine, chlorine, bromine and iodine.

Representative examples of phenylalkyl groups include benzyl, isopropylidene phenyl, butylidene phenyl, isopropylidene-4'-phenol, and butylidene-4'-phenol.

Specific examples of phenols which can be polymerized in accordance with the process of the present invention are phenol, 4-t-butylphenol, 4-n-butylphenol, 4-ethylphenol, cresol, p-phenylphenol, p-octylphenol, p-nonylphenol, p-hydroxybenzoic acid, 4-hydroxynaphthoic acid, p,p'-biphenol, 4-aminosalicylic acid, salicylic acid, methyl salicylate, ethyl salicylate, 4,4'-isopropylidenediphenol, ethyl 4-hydroxybenzoate, etc.

In one embodiment, a phenolic developer resin capable of reacting with an electron-donating color precursor and producing a visible image is represented by the formula (II):

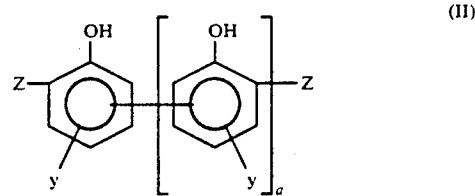

(II)

where n is greater than 2, the phenolic units of the resin are directly bonded to one another through positions ortho or para to the hydroxyl group, Y is not hydrogen and is present at a position meta or para (preferably para) to the hydroxyl group.

In accordance with another embodiment, the phenolic developer resin is represented by the formula (III):

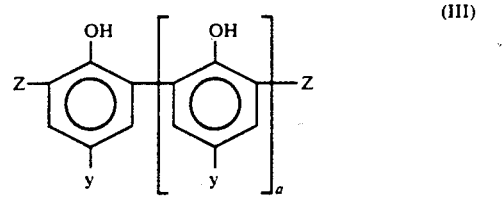

(III)

where n, Y, and Z are defined as in formula (II).

The phenolic resins can be homopolymers or copolymers, i.e., the individual Y or Z groups in a given phenolic developer resin may be the same or different and the Y groups may be located at different positions in accordance with the formula (II).

The phenolic developer resins may be metal-modified in a manner analogous to novolak developer resins to improve their reaction with color precursors and thereby improve the density and fastness of the image. For example, the phenolic developer resins can be modified by reaction with a salt of a metal selected from the group consisting of copper, zinc, cadmium, aluminum, indium, tin, chromium, cobalt, and nickel.

This modification can be made in an otherwise known manner. One method is by mixing and melting the resin with an alkanoate salt such as zinc propionate, zinc acetate, or zinc formate in the presence of an ammonium compound such as ammonium carbonate or ammonium acetate. The practice described in U.S. Pat. No. 4,173,684 can also be used.

The zinc-modified phenolic developer resins can also be formed by reacting zinc oxide or zinc carbonate and ammonium benzoate or ammonium formate with the resins in a manner analogous to the teachings in U.S. Pat. Nos. 4,165,102 and 4,165,103. Alternatively, the zinc-modified phenolic developer resins can be prepared by reaction with zinc chloride as shown in the examples below.

The metal content of the metal-modified phenolic developer resins should be more than 0.5 percent by weight and may range up to 25% by weight. Usually, a range of about 1.5 to 5 percent by weight is used.

In addition to chemically modifying the phenolic developer resins as described above, other means conventionally used in the art to improve the developing ability of phenolic developer resins, can be used in conjunction with the phenolic developer resins of the present invention. For example, acidic metal salts can be incorporated into coatings of the phenolic developer resins as described in U.S. Pat. Nos. 3,516,845 and 3,723,156. The phenolic developer resins of the present invention can also be used in combination with other phenolic developer resins or compounds and need not be used alone.

Recording materials utilizing phenolic developer resins to produce colored images from colorless or substantially colorless materials are well known. Specific examples of such recording materials include pressure-sensitive carbonless copying paper, heat-sensitive recording paper, electrothermographic recording paper, and the like. They are described in more detail in U.S. Pat. Nos. 2,712,507; 2,730,456; 2,730,457; 3,418,250; 3,432,327; 3,981,821; 3,993,831; 3,996,156; 3,996,405 and 4,000,087, etc. A photographic material has been developed which utilizes this method for forming colored images. See, for example, U.S. Pat. Nos. 4,399,209 and 4,440,846 to The Mead Corporation.

Recording materials can be prepared in a conventional manner. To provide a developer sheet, the phenolic developer resin may be dissolved in an appropriate solvent (typically acetone) and applied to the surface of the paper by blade or roll coating or the like. Alternatively, the developer resin may be used in the form of a resin grind analogous to the resin grinds described in U.S. Pat. No. 3,924,027 to Saito et al. For example, the resin may be pulverized and mixed with an organic high molecular compound such as starch or styrenebutadiene latex. This mixture is dispersed in water or a solvent that does not readily dissolve the phenolic developer resin or the high molecular compound and coated on an appropriate support.

The developer resin is usually applied in an amount of about 0.2 to 0.4 lbs. or resin/1300 sq. ft. (solids).

Where a self-contained recording material is desired, a mixture of the phenolic developer resin and microcapsules containing the developer can be coated upon a support as one layer, or the developer and the microcapsules can be applied in separate layers. For the preparation of photosensitive recording materials, see U.S. Pat. Nos. 4,399,209 and 4,440,846 which are incorporated herein by reference.

In addition to being useful as developer resins and as adhesives, phenolic resin products are useful in other applications. In particular, the lack of a methylene bridge imparts advantageous properties to the resins as counterparts. The resins should exhibit greater resistance to photolytic and thermal degradation, greater rigidity and greater conductivity making the resins potentially attractive for plasma resistance in photoresists, as conductive polymers, antioxidants for plastics, rubbers and the like, and as molding materials for high temperature applications. The higher density of functional hydroxy groups is being investigated for use in epoxy resin systems where higher crosslink densities should yield higher thermal deformation temperatures.

The resins produced in the present invention are also useful in composites analogous to epoxy resins. They are particularly useful in frictional composites such as brake linings, transmission bands, structural composites.

The process of the present invention is also useful in preparing lower molecular weight compounds such as dimers or trimers. Accordingly, in formula (II) and (III) above, the process should be useful in preparing compounds for which n is 1 or 2 as well as higher molecular weight compounds in which n is greater than 2.

In addition to being useful in preparing phenolic resins, soybean peroxidase and peroxidases from other legumes, rice and malvaceous plants are also believed to be useful in the following reactions: oxidative coupling of aromatic amines and indoles; oxidation of anions to free radicals (e.g., carboxlyates, cyanide, thiolates, sulfite, ascorbate); oxidation of metallic mercury; hydroxylation of aromatic phenols and amines; oxidation of anions to inium ions (e.g., iodide, thiocyanate); oxidation of phenols to quinone methides and aromatic amines to imines; formation of disulfides from thiols, sulfoxides from sulfides and halides; formation of superoxide from thiols and oxygen; dehalogenation of halogenated phenols and aromatic amines; depolymerization of lignin and coal; iodination of aromatics; cleavage of uricates and sugars; oxidation of olefins to alcohols; cleavage of aldehydes to acids and ketones; demethylation of N-substituted aromatic amines; and treatment of wastewater for contaminants phenols and/or aromatic amines (see Alberti and Klibanov, supra).

In addition to being useful in the reactions discussed above, soybean peroxidase and hulls harvested and treated using the techniques described herein may also be useful in other applications previously thought to require the use of more expensive enzymes including the following: as biocides in pulp and paper mill streams (see U.S. Pat. No. 4,478,363); in enzymatic bleaching of Kraft pulp (see Intl publ No WO 87/00564, Intl Appln No PCT/US86/01476, Eriksson, KE, Chem Abstr 112:219038h, Ander, P., Chem Abstr 112:212969d); as a catalyst in immobilization of leachable toxic soil pollutants (see Shannon, M.J.R., et al. Appl. Env. Microbiol (1988) 54:1719-1723); in medical diagnostics in coupling to antibodies and detection with leuco-dyes (see U.S. Pat. Nos. 3,694,207; 4,828,983; 4,778,753; EP 218,083); in quinone dye synthesis (see Czch pat CS 247,596 Bl); accelerated drying of lacquers (see Japn. Pat. 01163272); in synthesis of melanin-like dyes (see U.S. Pat. No. 4,609,544); in oxidative thickening of pectins (see U.S. Pat. No. 4,672,034); as bioamperometric sensors for phenol detection (see Bonakdar, M., Chem Abstr 112:90986j); in analytical determination peroxides (see Berlin, P., Chem Abstr 112:73352); as a bacteriacide to prevent tooth decay (see Grisham, M.B., Chem Abstr 112:117169j, Kessler, U.S. Pat. No. 4,476,108); in inactivation of mutagenic substances (see Chem Abstr 93:21203d, Japanese Patent 55037180); in treatments and compositions to promote wound healing (see U.S. Pat No. 4,503,037); in waste water treatment (see U.S. Pat No. 4,623,465, Science 221:259-261 (1983), Enzyme Microb Technol 3:119-122 (1981), Davis, S., Chem Abstr 112:222683v, Alberti and Klibanor, supra), as a preventative for artherosclerosis (see Khanin, AL Chem Abstr 82:68359x); in activation of commercial enzymes (see Tressel, P., BBRC 92:781-786 (1980)); in quantitation and detection of gums (see Dickmann, R.S., Chem Abstr 111:55931k); in bleaching of fabrics (see Kirk, O., Chem Abstr 112:101222k); in stabilization or removal of phenols in beer (see Giovanelli, G., Chem Abstr 112:156624y); and in solubilization of coal (see Scott, C.D., Chem Abstr 113:26681z).

Of the foregoing applications, the soybean enzyme and hulls are particularly useful in wastewater treatment where they can be substituted for horseradish peroxidase.

The invention is illustrated in more detail by the following non-limiting examples.

EXAMPLE 1

Purification and use of horseradish peroxidase 100 g of a Tannic Acid solution was dissolved in 900 ml of 0.1 M phosphate buffer of pH=6 to produce a 10% solution (W/V). The volume of the solution was adjusted with the phosphate buffer to 1000 ml. 200 ml of horseradish peroxidase solution from Finnsigar Biochemicals was stirred at room temperature and 20 ml of the 10% tannic acid solution was added over 5 minutes. The mixture was stirred for an additional 15 minutes and then poured into 800 ml of acetone with stirring. After 5 minutes the solution was filtered through a Whatman #4 paper filter. The precipitate was dissolved in 200 ml of water and centrifuged at 1500 Xg for 30 minutes. Following centrifugation, the supernatant was used as the source of enzyme in a biocatalytic process for preparing phenolic resin. At the end of the polymerization reaction, aqueous and organic phases separated spontaneously. The organic phase was filtered through diatomaceous earth to remove particles and then evaporated with steam to yield a light colored amber phenolic resin.

EXAMPLE 2 (COMPARISON)

The procedure of Example 1 was repeated except that the horseradish peroxidase was not treated with tannic acid prior to its use as a peroxidase enzyme in the polymerization reaction. At the end of the reaction a stable emulsion prevented separation of the aqueous and organic phases. The phenolic resin recovered from this reaction produced a red-brown resin. The phenolic resins produced in examples 1 and 2 were analyzed by HF gel-permeation and reverse phase chromatography which showed that the resins were very similar except for color.

EXAMPLE 3

Method of Harvesting Soybean Peroxidase: One kg of dry soybeans obtained from J.R. Kelly Company, Collinsville, Ill. was placed in a blender and homogenized in 5 1 of water. The homogenate was filtered through four layers of cheesecloth and the filtrate saved. To 500 ml of the filtrate was added 75 ml of 10% tannic acid in 0.1 M phosphate buffer. The mixture was centrifuged at 1500 Xg for 30 minutes and the supernatant saved. Protein in the supernatant was precipitated by pouring the supernatant into 3 volumes of acetone at room temperature. The acetone was decanted and the precipitate was dissolved in 500 ml of water. Protein contaminants were further removed by the addition of 2.5 ml of 50% $ZnCl_2$ in water. The Zn treated protein was centrifuged at 1500 Xg for 30 minutes and the supernatant was decanted. The supernatant was poured into 3 volumes of acetone to precipitate the Zn-treated protein. The acetone was decanted and the precipitate was dissolved in 100 ml of water and used as the source of soybean peroxidase enzyme.

Biocatalytic Polymerization of 4,4'-isopropylidenediphenol (Bisphenol A): The soybean peroxidase enzyme obtained above is employed as a biocatalyst in a normal polymerization of bisphenol A except that only 70% of the normal amount of enzyme is used (normal enzyme is from horseradish roots). 100 g of bisphenol A is dissolved in 60 ml of acetone and 140 ml of ethyl acetate. 3500 units of the soybean peroxidase at 14 units/mg protein (0.25g) are dissolved in 400 ml of deionized water. Both solutions are added to a one liter, three-necked round bottom flask and stirred at 300 rpm's. 67 ml of a 15% hydrogen peroxide solution is added over an approximately 6 hour period. Upon completion of the reaction, phase separation occurs spontaneously and the product is easily recovered from the organic phase by evaporation. The product shows the same distribution of polymer and same glass-transition temp Tg=83° C. as obtained when using horseradish peroxidase and bisphenol A except that no residual monomer is detected. Thus, using 2/3 the normal amount of enzyme, a 100% yield of bisphenol A polymer is obtained using the pre-treated soybean peroxidase.

EXAMPLE 4

A volume of a detergent (sodium dodecyl sulfate) is added to a solution of horseradish peroxidase to give a 2% final concentration of detergent (W/V). The protein is precipitated by pouring the mixture into 3 volumes of isopropanol. The precipitate is dissolved in a minimal volume of water and assayed for peroxidase. The treated peroxidase is mixed with bisphenol A dissolved in 20% acetone in the ratio of 50 units peroxidase per gram of bisphenol A per 6 ml of 20% acetone. A 15% hydrogen peroxide solution was added in the ratio of 0.18 ml per g of bisphenol A over a period of one hour. After one hour the mixture was centrifuged at 1500 Xg for 15 minutes and the bisphenol A resin recovered. The supernatent was used as the source of enzyme in a normal polymerization reaction.

EXAMPLE 5

Soybeans are cracked in a grinding mill, extracted with acetone, and soaked in water to loosen the hulls. The hulls float to the surface and are isolated by pouring them onto a screen. The hulls are homogenized in 0.4 M ammonium sulfate filtered through cheese cloth and the homogenate is separated into three samples which were treated as follows:

Sample 1: The homogenate is adjusted to 30% isopropanol (V/V), and slurried with activated carbon at 1% W/V concentration. The slurry is stirred for a few minutes after which the mixture is filtered through celite on a Whatman GF/F glass fiber filter (0.7 micron pore size). The filtrate is used as a source of purified soybean peroxidase.

Sample 2: The homogenate is slurried in water with 0.3% activated carbon. The slurry is stirred, filtered through celite and used as a source of purified soybean peroxidase.

Sample 3: The homogenate 20% acetone (W/V) and slurried with 1% activated carbon (W/V). The mixture was filtered through celite. The activated carbon was washed with 30% isopropanol in water (W/V) and the isopropanol wash was used as a source of purified soybean peroxidase.

In each of the three procedures, significant amounts of impurities are removed from the soybean peroxidase in an economical manner to allow the use of the purified enzyme in a wide variety of applications where these impurities might otherwise interfere.

EXAMPLE 6

Soybean seed hull extract was mixed with an equal volume of 20% t-butyl phenol in isopropanol. 0.5 volumes of water was added and the mixture centrifuged at 1500 Xg for 15 minutes. The aqueous layer was removed by siphoning and adjusted to 6-10% KCl solution W/V with solid potassium chloride. The treated extract was poured into 4 volumes of acetone. The acetone solution was centrifuged and decanted. The precipitate was dissolved in water to yield purified soybean peroxidase at 4M KCl concentration. The treated soybean peroxidase was used in the polymerization of bisphenol A to produce a low molecular weight polymer of bisphenol A.

EXAMPLE 7

The procedure of Example 6 was repeated using t-butyl phenol as the purifying agent in n-propanol to provide purified soybean peroxidase.

EXAMPLE 8

The procedure of Example 6 was repeated using bisphenol A as the purifying agent in isopropanol to provide purified soybean peroxidase.

EXAMPLE 9

The procedure of Example 6 was repeated using bisphenol A as the purifying agent in n-propanol to provide purified soybean peroxidase.

In each of Examples 7-9, the soybean peroxidase enzyme is used in the polymerization of bisphenol A to provide a bisphenol A resin similar to that obtained in Example 6 and 10. Examples 6-9 are useful with hulls isolated from aged beans (over 1 yr. old) or hulls contaminated with significant amounts of bean material as well as fresh hulls.

EXAMPLE 10

Horseradish root extract was mixed with an equal volume of 20% t-butyl phenol in isopropanol. 0.5 Volumes of water was added and the mixture centrifuged at 1500 Xg for 15 minutes. The aqueous layer was removed by siphoning and mixed with about 6-10% KCl solution. The treated extract was poured into 4 volumes of acetone. The acetone solution was centrifuged and decanted. The precipitate was dissolved in water to yield purified horseradish peroxidase. The treated horseradish peroxidase was used in the polymerization of bisphenol A to produce a low molecular weight polymer of bisphenol A.

EXAMPLE 11

The procedure of Example 10 was repeated using t-butyl phenol as the purifying agent in n-propanol to provide purified horseradish peroxidase.

EXAMPLE 12

The procedure of Example 10 was repeated using bisphenol A as the purifying agent in isopropanol to provide purified horseradish peroxidase.

EXAMPLE 13

The procedure of Example 10 was repeated using bisphenol A as the purifying agent in n-propanol to provide purified horseradish peroxidase.

In each of Examples 11-13, the horseradish peroxidase enzyme is used in the polymerization of bisphenol A to provide a bisphenol A resin similar to that obtained in Examples 5 and 9.

EXAMPLE 14

The economic and practical utility of soybean seed hulls was tested as a substitute catalyst in the synthesis of bisphenol A polymer, a well-established color developer which can be made in a predicable manner using free horseradish or soybean peroxidase in solution. Ground soybean hulls were obtained from Cargill, Inc. of Sidney, Ohio. The hulls were screened through a 30 mesh screen and the −30 mesh hulls were used in the following examples. The reaction conditions were 100g hulls added to 840 ml aqueous solution and mixed with 200g bisphenol A dissolved in 360 ml n-propanol. Fifteen percent hydrogen peroxide was added gradually over 2.5 hours until 60 mole percent was added. No peroxide excess was indicated by using starch-iodide test strips during the reactions. Stirring was at 300 rpm and the exothermic polymerization was allowed to proceed without temperature control. Typically, the temperature may reach a maximum of 40° C. At the end of the reaction, the mixture was centrifuged at 1,500xg for 10 minutes and the aqueous supernatant decanted. Occasionally, a 2-fold dilution with water is required for good separation on centrifugation. The polymeric resin and hulls were stirred with 1 liter ethyl acetate, recentrifuged and the supernatant filtered through a Whatman GF/F Glass fiber filter. The ethyl acetate was separated from the polymer by evaporation on a steam bath followed by a hot plate. The yield of resin was 60-90% of the starting monomer.

Having described the invention in detail and by reference to preferred embodiments thereof, it will be apparent that modifications and variations are possible without departing from the scope of the invention defined in the appended claims.

What is claimed is:

1. A method for the purification of a peroxidase enzyme comprising forming a solution of a peroxidase enzyme and a protein fixative selected from the group consisting of tannic acid, tannins, monolignols, fulvic acids, lignan, humic acids, melanoidins, proanthcyanidins, stilbenes, depsides, lignin model compounds, soluble suberin, flavonoids, dihydroxyphenyl compounds, kerogen, gallic acid esters, phenolic acids, gallic acid amides, hexahydroxydiphenic glucose estes, polymeric phenols, bis (hydroxyphenyl) sulfones, bitumens, soluble lignite extracts, sulfonated phenols and naphthols and their copolymers, melamineglyoxal/glyoxylate-phenol/naphthol condensates; peat euphorbia, cassia, rose, tea, grape and saxifragea; sulfonated extracts, and bark extracts, and graft copolymers derived from said extracts and syntans; adding a non-solvent for said enzyme to said solution to cause said enzyme to precipitate, and redissolving said enzyme and the peroxidase is recovered.

2. The method of claim 1 wherein said peroxidase enzyme is a soybean peroxidase.

3. The method of claim 2 wherein said protein fixative is tannic acid.

* * * * *